United States Patent
Moise et al.

(10) Patent No.: US 8,476,603 B2
(45) Date of Patent: Jul. 2, 2013

(54) IN-SITU PLANT ANALYSIS APPARATUS, METHOD FOR TRACKING THE STATE OR EVOLUTION OF A CULTURE AND METHOD FOR MANAGING VEGETABLE PROCESSING

(75) Inventors: Nicolae Moise, Gif sur Yvette (FR); Camelia Tinei-Moise, legal representative, Gif sur Yvette (FR); Andrei Nicolae Moise, legal representative, Gif sur Yvette (FR); Gwendal Latouche, Paris (FR); Zoran Cerovic, Paris (FR); Yves Goulas, Le Plessis Robinson (FR); Jean-Luc Ayral, Antony (FR)

(73) Assignees: Force-A, Orsay (FR); Centre National de la Recherche Scientifique, Paris (FR); Universite Paris Sud, Orsay (FR)

( * ) Notice: Subject to any disclaimer, the term of this patent is extended or adjusted under 35 U.S.C. 154(b) by 593 days.

(21) Appl. No.: 12/602,582

(22) PCT Filed: May 29, 2008

(86) PCT No.: PCT/FR2008/050941
§ 371 (c)(1),
(2), (4) Date: Dec. 1, 2009

(87) PCT Pub. No.: WO2008/152308
PCT Pub. Date: Dec. 18, 2008

(65) Prior Publication Data
US 2010/0181496 A1    Jul. 22, 2010

(30) Foreign Application Priority Data
Jun. 1, 2007 (FR) ....................... 07 03923

(51) Int. Cl.
*G01N 21/27* (2006.01)

(52) U.S. Cl.
USPC ............... 250/461.1; 250/365; 250/458.1; 250/336.1

(58) Field of Classification Search
USPC ........................................... 250/365
See application file for complete search history.

(56) References Cited

U.S. PATENT DOCUMENTS

| 4,804,850 A | 2/1989 | Norrish |
| 5,426,306 A * | 6/1995 | Kolber et al. .............. 250/458.1 |

(Continued)

FOREIGN PATENT DOCUMENTS

| DE | 10148747 | 4/2003 |
| NL | 9101639 | 1/1992 |
| WO | 02061405 | 8/2002 |

OTHER PUBLICATIONS

Agati, G. et al., "Nondestructive Evaluation of Anthocyanins in Olive (*Oleas europaea*) Fruits by in Situ Chlorophyll Fluorescence Spectroscopy", Journal of Agricultural and Food Chemistry, Feb. 10, 2005, pp. 1354-1363, vol. 53, No. 5, American Chemical Society, Washington, USA XP 002400872.

(Continued)

*Primary Examiner* — David Porta
*Assistant Examiner* — Djura Malevic
(74) *Attorney, Agent, or Firm* — Young & Thompson (57) ABSTRACT

A device for analyzing plants, by luminous excitation and fluorescence measurement, can be used on site without preparation of the plants. The device evaluates the content of a compound in the skin or epidermis of a plant. The geometry of the device is characterized by a direction of the excitation light rays and a direction of the fluorescence light rays which are non-collinear with each other. The device includes several sets of emitters of different wavelengths, each including several emitters, and makes it possible to measure a plurality of excitation-fluorescence combinations. A method for evaluating and monitoring the development and maturity of a crop, as well as a method for monitoring and controlling plant treatment are also described.

15 Claims, 4 Drawing Sheets

U.S. PATENT DOCUMENTS

| | | | | |
|---|---|---|---|---|
| 6,121,053 | A | * | 9/2000 | Kolber et al. .................. 436/172 |
| 6,260,994 | B1 | | 7/2001 | Matsumoto et al. |
| 6,563,122 | B1 | * | 5/2003 | Ludeker et al. ............ 250/458.1 |
| 2003/0048445 | A1 | | 3/2003 | Tokhtuel et al. |
| 2004/0007675 | A1 | * | 1/2004 | Gillispie et al. ........... 250/458.1 |
| 2005/0072935 | A1 | * | 4/2005 | Lussier ...................... 250/458.1 |
| 2005/0098713 | A1 | | 5/2005 | Holland |
| 2006/0249690 | A1 | | 11/2006 | Pfister et al. |

OTHER PUBLICATIONS

Goulas, Y. et al., "Dualex: A New Instrument for Field Measurements of Epidermal Ultraviolet Absorbance by Chlorophyll Fluorescence", Applied Optics, Aug. 10, 2004, pp. 4488-4496, vol. 43, No. 23, OSA, Optical Society of America, Washington, DC, USA XP002459288.

Belzile, C. et al, "An Operational Fluorescence System for Crop Assessment", Proceedings of the Spie—The International Society for Optical Engineering SPIE—Int. Soc. Opt., 2004, pp. 244-252, vol. 5271, No. 1, ENG, USA XP002464606.

Cerovic, Z. et al., "New Portable Optical Sensors for the Assessment of Winegrape Phenolic Maturity Based on Berry Fluorescence", In Precision Agriculture '07, 2007.

International Search Report mailed Nov. 18, 2008 form PCT/FR2008/050941.

French Search Report dated Jan. 17, 2008 from FR0703923.

* cited by examiner

IN-SITU PLANT ANALYSIS APPARATUS, METHOD FOR TRACKING THE STATE OR EVOLUTION OF A CULTURE AND METHOD FOR MANAGING VEGETABLE PROCESSING

The present invention relates to a device for analyzing plants, by luminous excitation and measurement of fluorescence, which can be used on site without preparation of the plants.

It also relates to a device for evaluating the content of a compound in the skin or epidermis of a plant.

Based on the use of such device, the invention also relates to a method for evaluating and monitoring the development and maturity of a crop, as well as a method for monitoring and controlling plant treatment.

The invention applies to the field of the analysis and evaluation of biological tissues, for example from plants and more particularly from crops within the context of so-called precision agriculture.

This term is used when it is sought to manage the state and development of a crop more precisely, for example over time or according to its local specificities within a geographical area. It may, for example, be a matter of optimizing the quality of the products obtained, or limiting the treatment or nutrients supplied to what is necessary or useful.

Until recently, the precise evaluation of the state of a plant, such as sugar content analysis or spectroscopy, relied on destructive analysis of the plant, most often in the laboratory. Such methods are complex and impractical. They cannot be used on site and do not allow adjustment to be carried out in real time.

The document US2005/0098713 proposes the evaluation of certain states of a crop by means of the pigments in a leaf, in particular chlorophyll or carotene, by reflectance measurement with modulation and phase detection.

This device uses a network of emission diodes and a network of detectors, arranged side by side, each emitting or receiving a beam collected and collimated by collimation optics.

This reflectance measurement technique has certain drawbacks, for example, great sensitivity to the state or cleanliness of the surfaces to be measured.

Another measurement device has been described in the publication of C. Belzile et al. entitled "An operational fluorescence system for crop assessment" which appeared in Proceedings of SPIE (vol 5271, pp 244-252, 2004) for evaluating certain states of potato plants, such as water or thermal stress, by measuring the fluorescence of the chlorophyll present in the leaves. This device uses two light-emitting diodes (LEDs) with excitation at different wavelengths, modulated differently to illuminate the leaves through a collimated optic, at a distance of 47 cm+/−7 cm. The fluorescence is measured through a collimated optic constituted by an assembly between a detector and filters corresponding to the fluorescence wavelengths to be measured, and the signal of which is demodulated with respect to the excitation sources.

This technology does not perform all the useful measurements, and has certain drawbacks. Each emission wavelength uses a single source produced by a single beam collimated by a lens. The detectors also use a collimation optic in order to receive the fluorescence generated.

In the state of the art a certain number of drawbacks persist, for example the space requirement, adjustment problems, and distance constraints due to the use of the collimated optics.

Moreover, the illumination of an object by such a source is not always uniform nor sufficiently constant, in particular in the case of objects with high relief, such as, for example, fruits or vegetables or blades of grass.

Moreover, the measurement of a single fluorescence at a determined wavelength is not sufficient to provide certain important information, such as the content of certain compounds characteristic of the development of the crop. Similarly, the use of only two fluorescence excitation wavelengths limits the use of such a device, whilst occupying a not insignificant volume in a device the characteristics of which make it necessary to mount it on a vehicle.

Moreover, when the value of a measurement is capable of developing within a very wide range, it is possible that not all the parts of this range can be measured with the same choice of wavelength.

Also, the use of a given wavelength may not function correctly when the chemical composition in the plant studied develops over time.

It is also useful to be able to have a device which is sufficiently compact to be able to be used manually, and sufficiently economical to be accessible to numerous users.

A purpose of the invention is to overcome the drawbacks of the prior art, and in particular to provide the following improvements:
  to allow non-destructive and rapid measurement on site,
  to allow measurement from only one side of the plant to be evaluated,
  to obtain good uniformity of the measurements on an object in three dimensions,
  to reduce or optimize the space requirement,
  to improve the simplicity of use and strength of the system,
  to improve the limits of the distance range which can be used for the measurement, allow measurement of the content of one or more fluorescent or non-fluorescent compounds, Another purpose of the invention is to improve or optimize the possibilities of monitoring plants over time or within a heterogeneous geographical zone, and in particular:
  to allow the evaluation of one or more development criteria exceeding the scope of a direct measurement,
  to optimize the continuity of measurement within a content range or to increase the width of such a measurable range,
  to optimize the continuity of measurement within a range of chemical compositions outside the content measured, for example according to the season, or to increase the width of such a measurable range.

For this purpose, the invention proposes a device for the non-destructive analysis of plants by fluorescence measurement, comprising:
  excitation means emitting excitation light in a determined wavelength band for generating a fluorescence in the tissues of a target zone,
  means of detection in a determined wavelength band for detecting the fluorescence thus generated,
  means for managing said excitation and detection means, and
  processing means arranged for dynamically correlating said excitation and detection means so as to provide a measurement of the fluorescence thus generated.

According to the invention, the excitation means and the detection means are arranged according to a determined geometry in order that the direction of the excitation light rays illuminating said target zone on the one hand, and the direction of the fluorescence light rays detected by the detection means on the other hand, are not collinear with each other.

In particular, the detection means receive the fluorescence light generated by the target zone without passing through optical convergence means.

Compared with the known techniques using collection and/or collimation optics, greater compactness as well as a wider range of measurement distance, lower cost and greater manufacturing simplicity are obtained. The detectors do not need to be very precisely adjusted in terms of position or orientation, and the device obtained is stronger, easier to use and maintain.

In the embodiment described hereafter, the measurement distance can be reduced to approximately 5 cm or 7 cm, and commonly to approximately 10 cm or 15 cm. Whereas there is a natural tendency to seek to increase the detection distance in order to save on mechanical movements, this short measurement distance can also have advantages. Thus, it allows a greater precision in the measurements, requires fewer targeting means or methods (such as image analysis), and reduces the influences of the ambient light.

Preferably, the excitation means include a set of emitters comprising at least two light emitters situated on either side of the detection means, illuminating the target zone in directions which are non-collinear with each other and in the same wavelength band.

This multiplicity of emitters combined with their position relative to the detector in particular allows more uniform illumination of the target, from different angles. For an object with heterogeneous relief, the zone seen and processed by the detector is thus illuminated in a more constant manner whatever its orientation in space.

In a preferred embodiment, the device according to the invention comprises:
 excitation means according to a plurality of different wavelength bands determined so as to allow a plurality of fluorescence measurements to be carried out, and/or
 detection means capable of detecting a fluorescence light in a plurality of wavelength bands determined so as to allow a plurality of fluorescence measurements.

It is thus possible to carry out several different fluorescence measurements with the same device.

Different fluorescence measurements are here defined as each corresponding to a combination of a determined excitation wavelength band associated with a determined fluorescence wavelength band. Thus, for example, a fluorescence measurement denoted $RF_G$ (Red Fluorescence—with Green excitation) corresponds to the measurement of fluorescence radiation generated in the red by an excitation in the green.

According to an advantageous aspect of the invention, the device also comprises means for selecting a fluorescence measurement from a plurality of possible measurements, said selection involving a selection of the excitation and detection means and of the treatment method to be implemented corresponding to the selected fluorescence measurement.

Therefore, a versatile and flexible tool is obtained, which is affordable and can be used for numerous uses: for example for experimentation or production, both on a small scale and on a large scale.

According to a feature of the invention, the management and processing means can then be arranged in order to automatically select and carry out, successively or alternatively, a plurality of different fluorescence measurements.

It is then possible to programme the acquisition of several different measurements in a single action by the user or in the course of a single movement.

In an advantageous embodiment, the device according to the invention comprises a portable case with its own power supply having a first face carrying user interface means and a second so-called measurement face directed in a measurement direction. This measurement face comprises:
 on the one hand, on its periphery a surface carrying the excitation means, and
 on the other hand, in its centre a part extending in the measurement direction.

This extension constitutes a detection module which contains at least part of the detection electronics and carries the detection means on its face on the side of the measurement direction, preferably at the same level as the end of the excitation emitters.

These characteristics help to reduce the space requirement, the weight and the cost of such a device, which can be produced in a portable form which can be used manually by a person on foot.

The excitation and detection means being assembled on a single face of the device, the measurement can be carried out on a single side of the plant to be analyzed, therefore without sampling or handling. It is therefore possible to carry out these measurements in a non-destructive manner, and sufficiently rapidly that they can be carried out in an on-the-fly manner while moving in front of a multitude of plants, such as in a plantation or a field or a lawn.

Measurement of a Compound

A preferred embodiment of the invention comprises such a device the management and processing means of which are arranged and programmed in order to provide at least two different fluorescence measurements, determined in order to be combined and correlated with each other by the processing means so as to calculate a measurement of the content of a component present in the target.

More particularly, the management and processing means are arranged and programmed in order to provide a measurement of the content of a chromophorous and non-fluorescent compound, by a screening effect on a luminous excitation generating a fluorescence of another compound situated further beyond the compound to be measured.

An example of a useful application is that which consists of measuring the content of compounds of the family of the anthocyanins or the flavonoids, in the skin of grape berries, the fluorescent compound situated beyond being chlorophyll.

In order to obtain a measurement remaining stable during measurements at variable distances, this measurement by screening effect comprises two different fluorescence measurements, generated in a fluorescent compound, for example chlorophyll. These two fluorescence measurements are chosen by using, generally for the excitation, wavelengths which are absorbed differently by the targeted chromophorous compound. From these measurements, the one whose excitation is absorbed by the targeted compound is called the "affected" measurement, and the other is called the reference measurement. By processes combining and correlating these two fluorescence measurements, it is possible to deduce the quantity of target compound having screened out the excitation light, by retaining a good independence with respect to the measurement distance.

The device characterized here is particularly well suited to carrying out this content measurement, since the latter requires two different fluorescence measurements.

In the same way, the invention also proposes a biological or agricultural management system including such an analysis device.

Such a system can in particular comprise means for communicating with digital position determination technology, or measurement control, or processing control, or computer communication means, or a combination of several of these means.

The invention also proposes a method for evaluating the state of a biological entity, and more particularly of a plant, utilizing such a device.

This method in particular makes it possible to monitor the development of a crop in time, by comparing a plurality of measurements carried out over time for a determined compound in the same plant or the same plot of land.

It also makes it possible to monitor the state of a crop within a geographical zone comprising a plurality of plots, by comparing a plurality of measurements carried out in said plots for a determined compound.

Within the context of an agricultural use, the versatility and flexibility of the device or system according to the invention also make it possible to determine one or more indices, which may be partly empirical, corresponding to a state of the analyzed plant and/or to its development.

Examples of Combinations of Fluorescence Measurements

In a simplified manner, the measurement of the content by screening effect is based on obtaining an absorbance value due to the compound to be measured, and corresponding to a formula of the type:

absorbance=log(reference fluorescence/affected fluorescence)

The combination of such a content measurement is denoted:

"(Reference Fluorescence$_{Excitation}$/Affected fluorescence$_{Excitation}$)"

Thus a measurement denoted "$FRF_R/FRF_G$" corresponds to:
- a reference measurement: far red fluorescence (FRF) generated by an excitation in the red;
- correlated with
- an affected measurement: far red fluorescence (FRF) generated by an excitation in the green.

Different embodiments of the invention make it possible, by providing such device with corresponding emitter and detector wavelengths, to measure in particular the following compounds or indices:

$FRF_B/FRF_G$: anthocyanins and certain carotenoids.
$FRF_A/FRF_G$: anthocyanins and certain carotenoids.
$FRF_R/FRF_G$: anthocyanins and certain carotenoids.
$BGF_{UV}/FRF_{UV}$: composite index which can fairly closely represent the anthocyanins content, and moreover exhibit good stability when the measurement distance varies. This index is sensitive to the presence of certain types of pathogen. By correlation with another measurement relating to the anthocyanins, it makes it possible to verify the presence or absence of pathogens, for example during harvest or for the adjustment of a treatment.

Moreover, this index is sensitive to the presence of broadleaf weeds of the dicotyledon type (e.g. white goosefoot) in a crop of the monocotyledon type (e.g. maize).

$YGF_B/FRF_B$: composite index which can represent the presence of lignin, cutin and other phenolic polymers, it has the advantage of requiring no excitation in the Ultra Violet, the emitters of which are often bulkier and have a smaller range than the arrays of RGB diodes commonly available.

$FRF_R/FRF_{UV}$: flavonoids.
$FRF_R/FRF_B$: composite index essentially based on the flavonoids, but also sensitive to the carotenoids, which it therefore makes it possible to detect in correlation with another measurement of the flavonoids.
$FRF_B/RF_B$: chlorophyll.
$FRF_A/RF_A$: chlorophyll.

The abovementioned bands correspond to the following wavelengths:
UV: 300-400 nm (ultra-violet), more particularly 360-390 nm
B: 400-470 nm (blue)
BGF: 400-500 nm (blue-green fluorescence)
G: 510-540 nm (green)
YGF: 520-570 nm (yellow-green fluorescence)
A: 590 nm (amber)
R: 620-650 nm (red)
RF: 670-695 nm (red fluorescence)
FRF: 705-800 nm (far red fluorescence)

Improvement in the Measurement Ranges

The versatility of the device according to the invention also allows improvement and optimization of the possible measurement ranges and of the continuity of the measurements in these ranges.

Thus, for the measurement of a determined compound by screening effect, when this compound is present in large quantities, the absorption of the excitation can be too significant for it to be possible to separate the fluorescence generated from the noise specific to the measurement conditions. The development of the measurement of fluorescence affected by the target compound then no longer reflects its content.

In response to this problem, the device according to the invention comprises the possibility of processing the reference measurement as an affected measurement using small variations of this measurement when it is slightly affected by the target compound. The device then comprises positioning and guidance means making it possible to maintain a constant measurement distance, for example a skirt surrounding the measurement face.

These guidance means advantageously comprise an extension projecting beyond the measurement face, which is sufficiently rigid to allow the user to bend the plants measured by resting lightly on top with these guidance means. The plants to be measured are thus rapidly and effortlessly brought to the right distance from the measurement face. This extension can be open-worked and surround part or all of the measurement face. In particular, the abovementioned skirt can be produced by a simple rigid or resilient lattice, for example made of resilient metal wire or moulded plastic lattice.

Thus, the user can measure numerous plants in quick succession, or even continuously, by simply passing in front of these plants while resting the guidance means lightly on the tips of these plants or on the surface of the plant cover that they constitute. He can thus cover the surface of a field of wheat by slightly flattening the ears in order to rapidly measure the tips of a large number of stalks. It is also possible to rapidly scan the foliage of a hedge, or the blades of grass in a lawn or grassland.

The mathematical result of the usual, so-called "canonical" formula then follows a descending curve whilst the compound content increases. The processing means then carry out a mathematical correction consisting of inverting the ratio between the affected fluorescence and the reference fluorescence. This inversion makes it possible to provide values continuing to increase, which means more to the user and makes it possible to construct a more ergonomic calibration in order to provide the compound content.

In order to provide a measurement without a priori knowledge of the compound content, the device can use another fluorescence measurement to determine whether or not the main measurement is saturated, for example the $BGF_{UV}/FRF_{UV}$ measurement in the case of the anthocyanins. In an embodiment comprising a set of amber light excitation emitters, the device can also use the $YGF_A/FRF_A$ measurement.

The power of the amber light sources then allows a measurement at a greater distance than with the UV sources described, for example up to approximately 1 m.

Another possibility is provided for exceeding the saturation threshold of the initial measurement of a compound, using a new excitation wavelength, different from the absorption peak of this target compound. The versatility of the device thus makes it possible to combine a third fluorescence measurement, for example for the anthocyanins by the $FRF_A/FRF_G$ measurement when the $FRF_R/FRF_G$ measurement is saturated.

Moreover, the variations in chemical compositions outside the measured content can affect the performances of this content measurement, for example by a change in the pH during development and according to the season.

The multiplicity of the possible measurement combinations thus makes it possible to pass from one combination to another, for example in the case of the anthocyanins between the three measurements $FRF_B/FRF_G$, $FRF_A/FRF_G$ and $FRF_R/FRF_G$.

Thus, in order to improve the continuity of a compound content measurement, or to extend the "external" chemical composition ranges where this measurement is possible, the device comprises the choice of use of one or more different fluorescence measurements, as a function of these measurement conditions. These possibilities are programmed into the processing means of the device, and allow better continuity of measurement over a wider range of compound measurement, without requiring new fluorescence measurements, and therefore with the same emission and detection means.

This choice can be recommended or automated, depending on the season or as a function of the results of a first measurement of content or of fluorescence, or as a function of information provided by another device.

Applications:

The invention has applications in numerous agricultural fields, or in the management of natural areas.

A typical use is the measurement of the flavonoids or anthocyanins content in the epidermis of the leaves or the skin of different types of vegetables or fruits.

Flavonoids and anthocyanins can often be associated with the nutritional value of fruits, for example apples.

Anthocyanins can often be associated with the maturity of a fruit, and more precisely to the phenolic maturation.

Another interesting use is the precise development of the state of an area of vegetation having a certain heterogeneity, for example in cartographic form. It may be a matter of wild areas such as natural parks, cultivated areas or maintained areas such as golf courses or stadia.

Other compounds, such as carotenoids, can be associated with the maturity of vegetables, for example lycopene in the case of tomatoes.

The invention proposes in particular implementing such a method for evaluating the maturity or the quality or the composition of the grape by measuring the content of at least one anthocyanin or flavonoid type compound in the skin of a fruit, and in particular of a grape berry or a bunch of grapes.

In the case of grapes, the measurement of the anthocyanins content (in particular in the case of red grapes) or of the flavonoids content (in particular in the case of white grapes) makes it possible to have a good so-called phenolic maturity index, without requiring chemical analysis. This phenolic maturity is in fact an important factor which can influence the quality of the wine obtained from this grape.

The invention thus makes it possible to have a better knowledge of the state or the requirements of a crop at different times in its development or in different plots, in particular in the case of a crop which is heterogeneous in terms of time or space. This knowledge makes it possible to organize the different operations, such as pruning, harvest, phytotherapeutic treatment or supply of nutrients, at the opportune moment.

Control of Treatment

Advantageously, the invention can be implemented in order to analyze, in an ad hoc fashion, a plurality of plants to be evaluated, as the measurement device moves through the crops, or conversely after harvest.

This evaluation can also make it possible to adjust in real time, as and when needed, the nature of an operation in progress or the quantity of treatment or nutrient utilized.

Thus, a use of the invention can be the adjustment of a fertilizing treatment as a function of the state of the plants evaluated, or the adjustment of a phytotherapeutic treatment as a function of the detection of pathogens and of their quantity.

Another use of the invention can be monitoring the quality of products after harvest, and controlling a selection or treatment during packaging.

Figure 1:
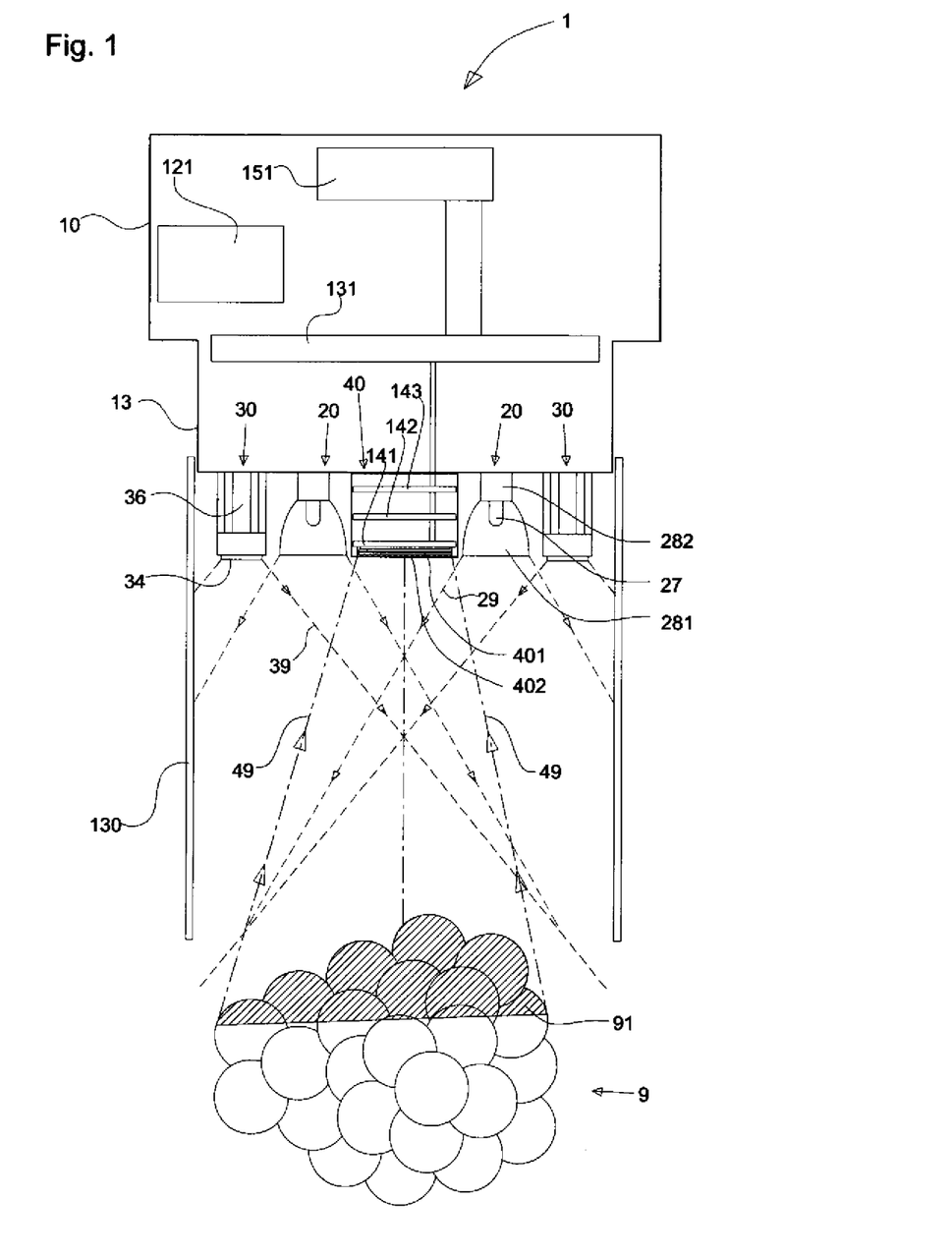
FIG. 1 diagrammatically represents a device according to an embodiment of the invention.
Figure 2:
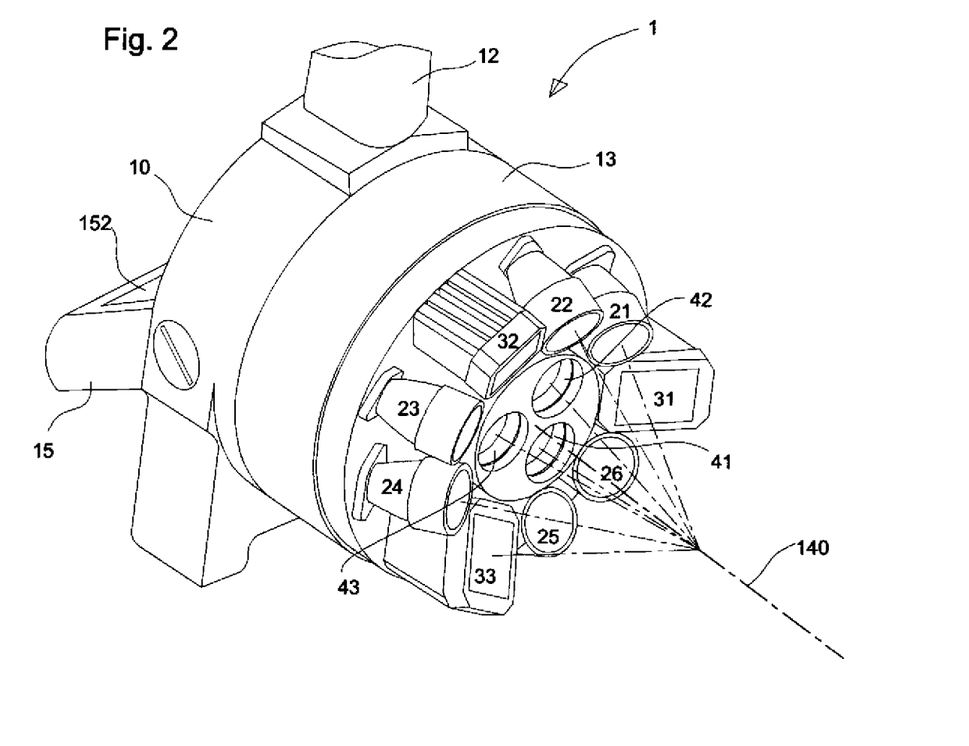
FIG. 2 is a perspective view, from the side of the measurement face, of a device according to an embodiment of the invention.
Figure 3:
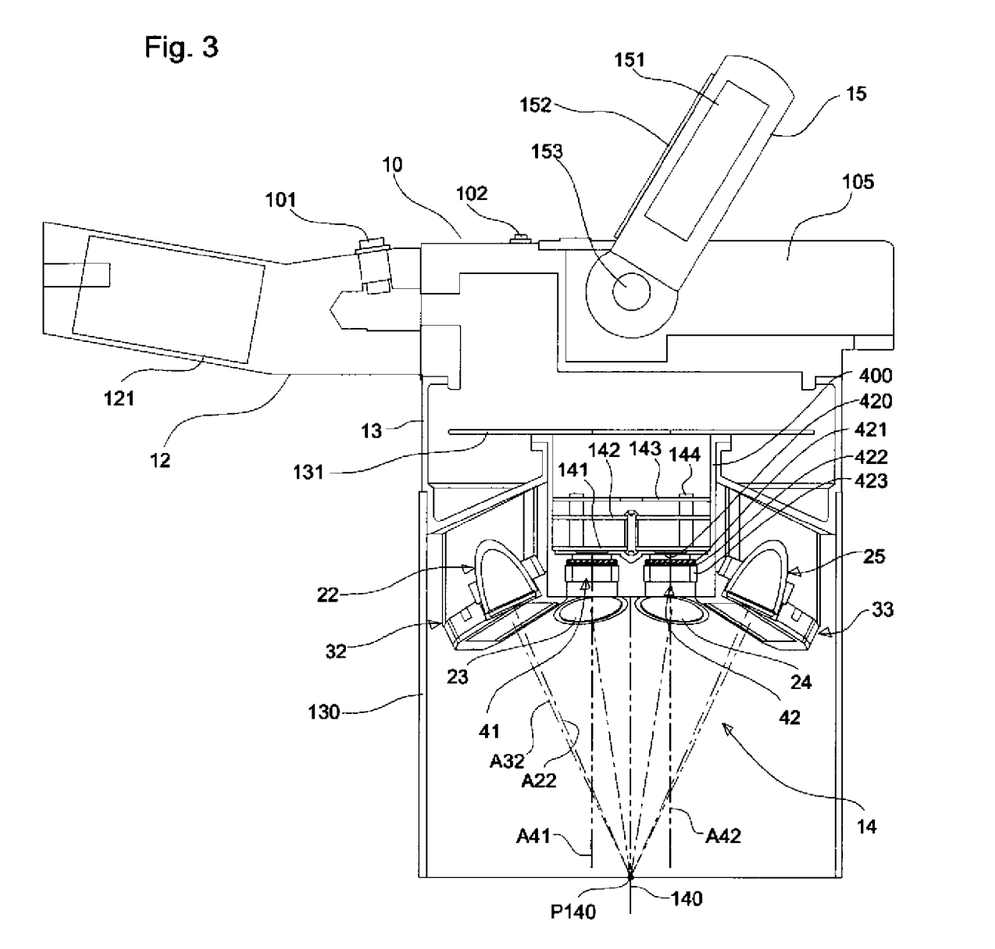
FIG. 3 is a simplified lateral cross-section of a device according to an embodiment of the invention.

Other characteristics and advantages of the invention will become apparent from the detailed description of an embodiment which is in no way limitative, and the attached drawings in which:

FIGS. 1 to 3 represent a preferred embodiment of the invention, as actually carried out and tested.

This embodiment is based on a portable case 10 and supplied by a battery 121 which is remote or integrated in the handle, provided with a measurement face 14 and a user interface comprising a screen 152 and controls such as buttons or keys 101 and 102. This case can be held by a part forming a handle 12 containing the replaceable battery 121 or the connector of the remote portable battery.

This case 10 also comprises a cylindrical part 13 extending towards the side opposite the interface and carrying the measurement face at its end. The measurement face 14 is surrounded by a shield 130 which is more or less opaque and possibly detachable, which makes it possible to reduce interference from ambient light and to provide a point of reference as to the optimum measurement distance relative to the measurement face 14.

This measurement face comprises a set 40 of detectors covering the fluorescence wavelengths to be measured. In the embodiment described here, this set 40 comprises three detectors 41, 42 and 43 adjacent to each other and grouped together in an equilateral triangle in the centre of the measurement face 14. These three detectors are oriented in directions parallel to each other around a detection axis 140, or very slightly convergent around this detection axis 140. Each of these detectors 41, 42 and 43 comprises a detection element, here a silicon photodiode 420 approximately 2 cm×2 cm, and detects the light in a determined wavelength band, blue-green, red and far red respectively. This detection band is obtained by a coloured or high-pass filter and an interferential filter. The combination of these two types of filter allows better filtration which may be necessary, in particular to prevent the detectors receiving radiation emitted by the excitation sources.

It should be noted that the detectors directly receive the fluorescence to be measured, without using collection, convergent or collimated optics. Each detector requires only a single detection element, the photodiode 420 (FIG. 3), chosen to be large enough to obtain a good sensitivity which makes it possible to dispense with collection optics. This detection element thus receives radiation 49 originating from all of the target zone 91 illuminated by the excitation emitters.

This arrangement makes it possible to use relatively simple detection elements, and avoid the need for collection optics. Further to the savings on the cost of the optics, the size requirement, regulation and field depth constraints are also avoided.

The measurement face 14 has a concave conical peripheral surface carrying several sets of emitters, which can emit excitation light in different wavelengths, distributed in a circle around the set 40 of detectors.

These emitters comprise a set of ultraviolet emitters 20 comprising six UV emitters 21 to 26, distributed at 120° in three groups of two adjacent emitters, in a circle around the set of detectors 40.

Each of these sources comprises a source, here an ultraviolet LED 27, placed in a parabolic reflector 281 forming a beam of approximately 30°. The reflectors are mounted on a base 282 determining the position of their beam with respect to the detection axis 140. Alternatively, the UV emitters can also use a dioptric or catadioptric device to improve the convergence of the beam emitted.

The emitters also comprise a set of visible light emitters 30, comprising three emitters 31, 32 and 33 distributed at 120° around the set 40 of detectors in the same circle as the set of UV emitters 20 and intercalated with the UV emitters. Each of these visible light emitters comprises a source comprising an array of intercalated red-, green- and blue-coloured LEDs, incorporated in a common component 34 with sides measuring approximately 4.5 cm and with a power of 3×15 W, and covered by a plate of transparent plastic forming an array of convergent micro-lenses. This common component 34 is mounted on a block 36 forming a radiator, the shape of which determines the orientation of the source with respect to the detection axis 140. The emitter also comprises a wide bandpass coloured filter, making it possible to restrict the emissions in the wavelengths used for the detection of fluorescence, in particular towards the far red.

As an alternative to the RGB (red-green-blue) sources described here, monochrome excitation sources can also be used, for example amber-coloured sources in the form of a high-power monochrome LED array, of the order of 200 W continuously.

The excitation emitters are oriented so as to obtain uniform illumination of the target zone 91, even when it is a heterogeneous object and/or three-dimensional.

In embodiments for short-distance applications, for example using UV excitation, the beams of the emitters are oriented so as to converge towards the axis or the axes A41, A42 and A43 of the detectors 41, 42 and 43. More particularly, the axes A22, A32 of the excitation beams intersect with each other and with the detection axis 140 at the same point P140, at an optimum distance for the measurement. In the embodiment described, the convergence point P140 is situated between 10 and 20 cm from the set 40 of detectors, for example approximately 15 cm.

The fact that the beams emitted are not collimated and exhibit a certain opening or divergence makes it possible to limit the constraints affecting the measurement distance. In fact, as the target, here a bunch of grapes 9, is situated inside the beams 29 and 39 of the emitters, it is illuminated homogeneously over its different faces directed towards the set 40 of detectors. The fluorescence 49 emitted towards the detectors is thus sufficiently stable and homogeneous to provide true measurements of the measured zone 91.

Thus, although the measurements using the UV emitters are made at a distance of approximately 15 cm, the measurements using only the visible light emitters can be carried out at greater distances, even up to approximately 1 m, for example for a measurement of the anthocyanins.

In other embodiments, the beams from the emitters can be oriented so as to be parallel to the detection axis, for example for applications with measurement at a significant distance.

FIG. 3 illustrates more particularly the structure of the device in this embodiment of the invention. The cylindrical part 13 of the case contains an electronic card 131 which is substantially annular, comprising power-supply circuits for the excitation sources, the management circuit of the excitation pulses and a circuit producing a current generator.

The detectors, and accompanying electronics, are grouped together in a cylindrical detection module 400, placed on the measurement face 14 in the centre of the circle formed by the excitation emitters and extending in the direction of the target to be analyzed. The outer face of this cylinder carries the three detectors 41, 42 and 43.

This arrangement makes it possible to place the detectors substantially at the same level as the ends of the emitters in order for them to have a wide reception field and thus makes it possible to get close to the target.

The detection module 400 comprises three small electronic cards 141, 142, 143 essentially analogue, substantially circular, stacked along its longitudinal axis, fixed and spaced out by small columns 144.

The first small electronic card 141, situated on the side of the outer face of the detection module 400, carries the detection elements, here silicon photodiodes. For each of these detectors, the silicon photodiode 420 receives the light to be detected through a coloured or high-pass filter 421 and an interferential filter 422 detachably fixed by a retaining nut 423 in a 25.4 mm cylindrical opening, which can thus receive standard 1 inch or 25 mm filters.

Moving away from the measurement face 14, the second small electronic card 142 carries the circuits and amplifiers carrying out rejection of the ambient light by a negative feedback loop.

The third small electronic card 143 carries circuits and components containing in particular track-and-hold units.

The detection module 400 constitutes a compact assembly which can be removed from the case 10, for example for maintenance or to be replaced by a camera module or a module including one or more optical waveguides.

This detection module is connected, through the opening in the large electronic card 131, to a processing module 151 situated on the side of the interface and comprising all or part of the processing means: in particular an acquisition unit and calculation means.

This processing module is contained in a part 15 of the case carrying the screen 152, which can be inclined for good readability, and retracted into a compartment 105 inside the case 10. This processing module can comprise a detachable connection which allows it to be exchanged easily, for example for updating or a change in function.

The electronics 131 linked with the excitation, and 141 to 143 linked with the detection, and the processing module 151 are thus arranged in different and separate electronic modules, allowing simplified maintenance. These modules are moreover separated by a certain distance, here two centimeters and typically at least 1.5 cm, which allows better dissipation of the heat generated and limits the risks of interference between the circuits that they comprise.

In the embodiment described here, the detection is synchronized with the excitation which is emitted by the excitation emitters. An excitation frequency of 1 kHz with 20 microsecond pulses has been used with success, and allows processing in real time as going along while covering the site. The different fluorescence measurements necessary for the establishment of the content or programmed index are interleaved within the measurement period.

Thus the management and processing means are arranged in order to:
  emit a control signal for controlling the emitters by pulses,
  detect the fluorescence peaks generated by these pulses, an amplification within the detectors produces the rejection of the ambient light by a negative feedback loop,
  control, for example by the same control signal, the processing of the detected fluorescence peak, for example, by means of track-and-hold units; and
  supply an analogue measurement of the fluorescence measurement to the acquisition unit.

In other embodiments, a synchronous detection is provided, using phase modulation between the excitation and the detection. The management and processing means are then arranged in order to:
  control the emitters according to a frequency including a phase modulation,
  process the fluorescence detection signal in phase demodulation and provide the fluorescence measurement.

Figure 4:
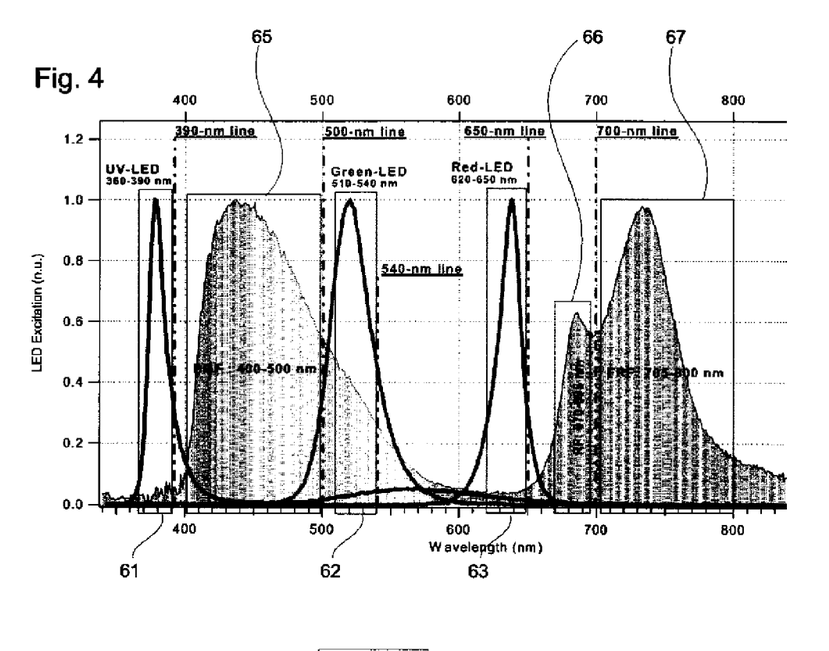
FIG. 4 represents a spectral diagram of the wavelengths utilized in a device according to an embodiment of the invention.

FIG. 4 represents the spectral diagram of the excitation wavelengths 61, 62 and 63 and of fluorescence detection wavelengths 65, 66 and 67 in the embodiment tested.

The device according to the invention has numerous applications, in particular in the field of agriculture or maintenance of green spaces and scientific research into plants.

This combination has made it possible to monitor and evaluate the development of the grape and its phenolic maturity by measurement of the anthocyanins in the case of red grapes and flavonoids in the case of white grapes.

These tests were carried out weekly from July to October on three varieties, Pinot Noir, Pinot Meunier and Chardonnay, in the Fort Chabrol experimental vineyard at Epernay in Champagne.

The results of these tests were verified by chemical analysis of the anthocyanins and the sugar content in °Brix, and are disclosed by the present inventors in a publication in progress, (Z. Cerovic et al. "New portable optical sensors for the assessment of winegrape phenolic maturity based on berry fluorescence", In Precision Agriculture '07, 2007).

With the same device, the measurements based on the blue-green fluorescence under UV excitation (i.e. $BGF_{UV}/FRF_{UV}$) can moreover be correlated with the results based on other fluorescences (for example $FRF_G/FRF_R$) in order to monitor the absence or presence of pathogens before or during harvest.

Figure 5:
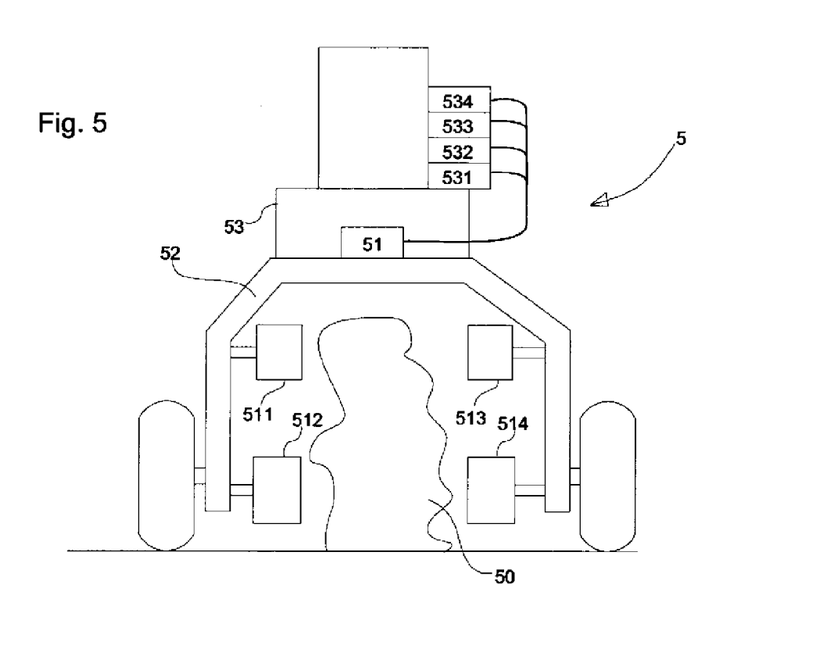
FIG. 5 is a diagram illustrating an implementation of a system according to an embodiment of the invention.

As illustrated in FIG. 5, other embodiments are possible, which comprise a system 5 including one or more analysis devices 511 to 514, mounted on a structure 52 with a shape and dimensions provided in order to be drawn by a vehicle 53 along a large area of vegetation, for example in order to continuously monitor and analyze a row of vines 50, on several levels and on both sides. These analysis devices 511 to 514 can each comprise only part of the means utilized, for example only the emitters and detectors part as well as their management means, and be centralized on a single processing module 51.

This processing module 51 can also be incorporated into, or communicate with, one or more computerized means such as position determination technology means 531, or means of control of the measurements 532, or control means 533 for a processing carried out as and when needed, or means of communication 534 with one or more other systems.

Other embodiments can be produced based on different types of vehicles brought in to cover the area to be treated or evaluated, for example on a lawnmower, or on an individual cart for transporting golf clubs.

In the present description, it should be noted that the concept of a crop must not understood in a too restrictive manner and can perfectly well include any plants which are monitored and/or maintained, even if they do not produce harvests, such as turf, or have not been planted artificially such as a monitored or maintained natural area.

Of course, the invention is not limited to the examples which have just been described and numerous adjustments can be made to these examples without exceeding the scope of the invention.

The invention claimed is:
1. Method for non-destructively measuring the content of at least one compound in a plant located in air, comprising:
  locating a device proximate said plant to establish a non-contacting, spaced apart air distance of less than 20 cm between a target zone (91) of said plant and a detection means (40, 41, 42, 43) of said device; and
  measuring the content of the at least one compound in said plant,
  wherein said device (1) comprises
    excitation means (20, 30) emitting excitation light in a determined wavelength band (61, 62, 63) for generating a fluorescence (49) in the tissues of a target zone (91),
    the detection means (40, 41, 42, 43) being configured in a determined wavelength band (65, 66, 67) for detecting the fluorescence thus-generated,
    means for managing said excitation and detection means, and
    processing means arranged for dynamically correlating said excitation and detection means so as to provide a measurement of the fluorescence thus generated, wherein,
  the excitation means is according to a plurality of different wavelength bands and the detection means is capable of detecting a fluorescence light in a plurality of wavelength bands (65, 66, 67), said wavelength bands being determined so as to make it possible to carry out a plurality of fluorescence measurements;
  the excitation means and the detection means are arranged according to a determined geometry in order that the direction of the excitation light rays (29, 39) illuminating said target zone (91) on the one hand and the direction of the fluorescence light rays (49) detected by the detection means on the other hand are not collinear with each other; and
  the excitation means include a set of emitters comprising at least two light emitters (21, 24) situated on either side of the detection means or distributed around said detection means (41, 42, 43), and illuminating the target zone (91) in the same wavelength band.

2. Method according to claim 1, wherein, said locating and measuring steps are performed in a vegetation area on a plurality of plants, said vegetation area being one of an agricultural field, a natural area, a plantation, a field, and a lawn, and said measuring step is performed in an on-the-fly manner.

3. Method according to claim 1, further comprising making a measurement in an on-the-fly manner of a plurality of plants, obtained by moving a guidance means (130) in contact with the tips of said plants, or of a plant cover which they constitute, with a sufficient pressure of said guidance means to bend the majority of said tips and thus obtain a regular measurement for the majority of said plants measured.

4. Method according to claim 1, wherein said measurement step includes evaluating a maturity or quality or composition of fruits or vegetables by measurement of the content of at least one anthocyanin or flavonoid or carotenoid type compound in the skin of said fruits or vegetables.

5. A device (1) for the non-destructive analysis of plants by fluorescence measurement, comprising:

excitation means (20, 30) emitting excitation light (29, 39) in first plural different wavelength bands (61, 62, 63), without contact with a target zone (91) of a plant located in air, the target zone of the plant being spaced apart from the excitation means by an air space, the excitation light being emitted, through the air space towards the target zone, in the first plural determined wavelength bands, the excitation light being suitable for generating a fluorescence (49) in tissues of the plant in the target zone (91) illuminated by the excitation light;

detection means (40) for directly receiving the fluorescence light (49) thus generated in each of second plural different wavelength bands (65, 66, 67), the detection means being free of contact with the plant and separated from the plant by the air space, and processing means arranged for dynamically correlating said excitation and detection means so as to provide a measurement of the fluorescence light thus generated, wherein, the excitation means and the detection means are arranged according to a determined geometry in order that the direction of the excitation light (29, 39) illuminating said target zone (91) and the direction of the generated fluorescence light (49) detected by the detection means are not collinear with each other, and the excitation means include a set of at least two light emitters (21, 24) emitting light in a common wavelength band, the at least two light emitters (21, 24) situated on opposite sides of the detection means (41, 42, 43) or distributed around said detection means, the light emitters illuminating the target zone (91) with the emitted light in the common wavelength band from opposite sides or from distributed positions of the detection means and through the air space towards the target zone of the plant.

6. Device according to claim 5, characterized in that the detection means (40) comprise at least one detector (41, 42, 43) receiving the fluorescence light (49) generated by the target zone (91), characterized in that said detector comprises a silicon photodetector (420) and at least one optical filter (421) for selecting the fluorescence band of interest and receives a fluorescence light (49) generated by all of the target zone (91).

7. Device according to claim 5, characterized in that it comprises means for selecting a fluorescence measurement from a plurality of possible measurements, said selection involving a selection of the excitation and detection means and of the processing method to be implemented corresponding to the selected fluorescence measurement.

8. Device according to claim 7, characterized in that the processing means are arranged in order to automatically select and carry out, successively or alternatively, a plurality of different fluorescence measurements.

9. Device according to claim 7, characterized in that the processing means are arranged in order to provide at least two different fluorescence measurements, determined in order to be combined and correlated with each other by the processing means so as to provide a measurement by screening effect of the content of a non-fluorescent chromophorous component present in the target.

10. Device according to claim 5, characterized in that the excitation means comprise one or more sources (27) based on at least one light-emitting diode (LED) surrounded by a convergence reflector (281).

11. Device according to claim 5, characterized in that it comprises a portable case (10) with its own power supply (121) having a first face carrying user interface means (152, 101, 102) and a second so-called measurement face directed towards a measurement direction, this measurement face comprising on the one hand on its periphery a surface carrying the excitation means and on the other hand in its centre a part (400) extending in the measurement direction, containing at least part of the detection electronics and carrying the detection means on its face on the side of the measurement direction.

12. Device according to claim 11, characterized in that at least one excitation emitter (30) comprises a plurality of LEDs incorporated in a common component (34), said excitation emitter (30) being fixed on a radiator element (36) the shape of which determines the position and orientation of said emitter.

13. Device according to claim 5, characterized in that the processing means are arranged in order to:

control the emitters by pulses, detect the fluorescence peaks generated by these pulses by means of amplified detectors which carry out the rejection of the ambient light by a negative feedback loop, process the fluorescence signal detected and provide the fluorescence measurement.

14. Device according to claim 5, characterized in that the processing means are arranged in order to:

control the emitters according to a frequency including a phase modulation, process the fluorescence detection signal in phase demodulation so as to obtain the rejection of the ambient light and provide the fluorescence measurement.

15. Device according to claim 5, characterized in that it comprises a shield or skirt (130) surrounding its measurement face (14) and producing guidance means or reference means of the measurement distance.

\* \* \* \* \*